United States Patent
Jie

(10) Patent No.: US 10,617,221 B2
(45) Date of Patent: Apr. 14, 2020

(54) TARGET HEATING METHOD AND SYSTEM WITHIN A DESIGNATED SPACE

(71) Applicant: Hui Jie, Shanghai (CN)

(72) Inventor: Hui Jie, Shanghai (CN)

(*) Notice: Subject to any disclaimer, the term of this patent is extended or adjusted under 35 U.S.C. 154(b) by 307 days.

(21) Appl. No.: 15/513,864

(22) PCT Filed: May 25, 2016

(86) PCT No.: PCT/CN2016/083267
§ 371 (c)(1),
(2) Date: Aug. 17, 2017

(87) PCT Pub. No.: WO2016/197820
PCT Pub. Date: Dec. 15, 2016

(65) Prior Publication Data
US 2017/0295947 A1    Oct. 19, 2017

(30) Foreign Application Priority Data

Jun. 8, 2015 (CN) .......................... 2015 1 0304408

(51) Int. Cl.
*A47C 21/04* (2006.01)
*A61N 5/06* (2006.01)
(Continued)

(52) U.S. Cl.
CPC .......... *A47C 21/048* (2013.01); *A47C 21/003* (2013.01); *A47C 21/04* (2013.01);
(Continued)

(58) Field of Classification Search
CPC ..... A47C 21/04; A47C 21/046; A47C 21/048; A47C 21/003; A61N 5/0625;
(Continued)

(56) References Cited

U.S. PATENT DOCUMENTS 4,832,029 A * 5/1989 Koch ....................... A61N 5/06
362/130
5,162,038 A * 11/1992 Wilker ................... A61G 11/00
119/306

(Continued)

OTHER PUBLICATIONS

Promolife Infrared Light Therapy Bed—https://www.promolife.com/promolife-infrared-light-therapy-bed/ (Webpage) (Year: 2019).*

*Primary Examiner* — Peter M. Cuomo
*Assistant Examiner* — David R Hare
(74) *Attorney, Agent, or Firm* — Wang Law Firm, Inc.

(57) ABSTRACT

A heating system includes a sensing and tracking module to sense length in at least one dimension of an object to-be-heated in a previously determined area. A light source module has at least one light source that can change its lighting direction and can also change its beam angle e along the at least one dimension. A control module is provided for regulating light emitted by the light source module onto the to-be heated object along the at least one dimension to match with the length of the to-be-heated object based on the length sensed by the sensing and tracking module. The heating system described above and a bed incorporated having this kind of heating system may automatically adjust its output power according to the physical characteristics of the object to-be-heated to avoid heating unrelated object, area or space so as to ensure high energy efficiency.

17 Claims, 1 Drawing Sheet

(51) Int. Cl.
*H05B 3/00* (2006.01)
*A61F 7/00* (2006.01)
*A61B 5/01* (2006.01)
*A47C 21/00* (2006.01)
*H05B 1/02* (2006.01)

(52) U.S. Cl.
CPC .......... *A61B 5/01* (2013.01); *A61F 7/00* (2013.01); *A61N 5/0625* (2013.01); *H05B 1/02* (2013.01); *H05B 3/0033* (2013.01); *H05B 3/0071* (2013.01); *A61F 2007/0094* (2013.01); *A61F 2007/0096* (2013.01); *A61N 2005/0637* (2013.01)

(58) Field of Classification Search
CPC .... A61N 2005/0627; A61N 2005/0626; A61N 2005/0637; H05B 1/01; H05B 1/02; H05B 3/0071; H05B 3/0033; A61F 7/00; A61F 2007/0094; A61F 2007/0096; A61B 5/01
See application file for complete search history.

(56) References Cited

U.S. PATENT DOCUMENTS

| | | | |
|---|---|---|---|
| 5,948,303 A * | 9/1999 | Larson | G05D 23/1905 126/205 |
| 6,673,007 B2 * | 1/2004 | Salmon | A61G 11/00 600/22 |
| 6,679,830 B2 * | 1/2004 | Kolarovic | A61G 11/00 600/22 |
| 6,718,128 B2 * | 4/2004 | Meyer | A61F 7/00 392/412 |
| 6,719,780 B1 * | 4/2004 | Salmon | A61F 7/00 607/108 |
| 8,160,718 B2 * | 4/2012 | Khodak | A61B 5/01 600/22 |
| 9,545,524 B2 * | 1/2017 | Maass | A61N 5/0618 |
| 9,873,308 B2 * | 1/2018 | Moench | B60H 1/00742 |
| 2004/0068305 A1 * | 4/2004 | Bansal | A61N 5/0621 607/89 |
| 2005/0073839 A1 * | 4/2005 | Pederson | A61M 21/00 362/230 |
| 2011/0245583 A1 * | 10/2011 | Vyasarao | A61G 11/00 600/22 |
| 2012/0113621 A1 * | 5/2012 | Lee | H01L 33/54 362/97.1 |
| 2012/0239119 A1 * | 9/2012 | Vyasarao | A61N 5/0625 607/88 |
| 2013/0066403 A1 * | 3/2013 | Giraud | A61B 18/203 607/89 |
| 2013/0259456 A1 * | 10/2013 | Viswanathan | F24D 13/00 392/407 |
| 2013/0274840 A1 * | 10/2013 | McLeod | A61F 7/00 607/100 |
| 2014/0301724 A1 * | 10/2014 | Graham | H05B 3/0071 392/407 |
| 2015/0028114 A1 * | 1/2015 | Rosen | G05D 23/1919 236/51 |

* cited by examiner

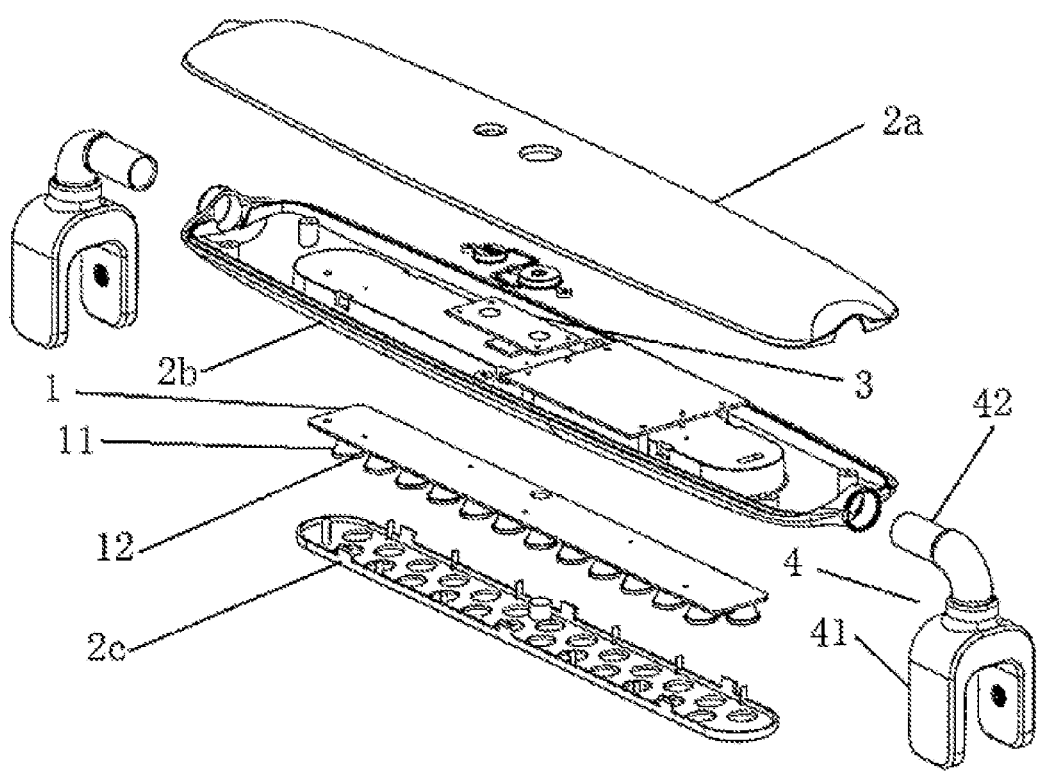

TARGET HEATING METHOD AND SYSTEM WITHIN A DESIGNATED SPACE

CROSS REFERENCE

This application is a national phase entry of PCT/CN2016/083267, filed on May 25, 2016, and claims the benefit of Chinese application "TARGET-HEATING METHOD AND SYSTEM WITHIN A DESIGNATED SPACE", filed on Jun. 8, 2015, bearing the serial number No. 2015103044082. The entirety of the content thereof is herein incorporated with reference.

TECHNICAL FIELD

The preferred embodiment of the present invention is related to a field of automatic temperature control and, more particularly, to a heating system and a bed having the heating system therein.

BACKGROUND OF THE INVENTION

Nowadays, temperature control is basically based on air conditioner and electromagnetic waves. However, both methods suffer from problems of energy waste and low energy efficiency.

Taking the air conditioner as an example, the air conditioner regulates the air temperature inside the room by undergoing heat exchange with the air inside the room. In practice, when the room temperature needs to be risen up, an air conditioner will heat up the air inside the room and release the heated air into the room, which will heat up all objects inside the room and consequently lead to a waste of energy, e.g., the refrigerator that shall be kept cold is also heated. In addition to low efficiency, air conditioner also suffers from another problem of long response time. It can only slowly heat up the certain space as a whole.

Another technology involving heating is, for example, the "bathroom-master", which can use the electromagnetic wave generated by high temperature materials to heat up the subject. The fact is that the bandwidth of the electromagnetic wave generated by the bathroom master is large, generally bigger than 100 nm and the to-be-heated subject has low absorbing coefficient to some wavelength of the electromagnetic wave, which results in a waste of energy since some energy is wasted to produce the electromagnetic wave that is difficult to be absorbed by the to-be-heated object. Additionally, the bathroom master also generates massive visible light and ultraviolet, of which the visible light will cause glaring, and make human eyes uncomfortable. The ultraviolet may even cause injury to human bodies and therefore unhealthy.

Another problem of using electromagnetic wave for heating is that the emission direction and beam angle cannot be adapted to the shape of the to-be-heated object, causing a portion of the electromagnetic wave is not used to heat up the to-be-heated object and therefore wasted. For example, the bathroom floor and the wall are heated as well.

It is because this kind of drawbacks existed in the current heating method and devices, a kind of more efficient heat generating device, which will target the to-be-heated object to raise its temperature while avoid heating up untargeted object or space is highly wanted so as to ensure higher energy efficiency.

SUMMARY OF THE INVENTION

It is an objective of the preferred embodiment of the present invention to provide a heating system and a bed including the same heating system to overcome the problem of energy waste and the harm done by the generating of harmful electromagnetic wave in the conventional methods as well as devices.

Another objective of the preferred embodiment of the present invention is to provide a heating system characterized in that the heating system has the following:

a sensing and tracking module for sensing length in at least one dimension of an object to-be-heated object in a predetermined area;

a light source module having at least one light source that can tune its light emitting direction and also can tune its beam angle along at least one dimension; and a control module for regulating light emitted by the light source module onto the to-be heated object along the at least one dimension to match with the length of the to-be-heated object based on the length sensed by the sensing and tracking module.

Preferably, the sensing and tracking module has a distance measuring unit for measuring distance between the to-be-heated object and the light source module. The control module calculates and regulates the light direction and the light beam angle from the light source module along at least one dimension based on the length of the to-be-heated object in the dimension and the distance between the light source module and the to-be-heated object.

Preferably, the light source module has a lens or a lens set. The lens or lens set is used for shaping the light from the light source module into a desired beam angle and/or intensity distribution.

Preferably, the intensity distribution is a Batwing beam pattern or Lambertian pattern.

Preferably, the wavelength of the light for heating from the light source module is between 900 nm-5000 nm.

Preferably, the light source module is an infrared light emitting diode chip.

Preferably, the control module calculates the needed intensity distribution to evenly heat the to-be-heated object based on the length in at least one dimension of the to-be-heated object and the distance between the to-be-heated object and the light source module, which is sensed by the sensing and tracking module, and also regulates the light source module and/or lens or lens set to reach the desired light intensity distribution.

Preferably, the to-be-heated object is movable and the sensing and tracking module includes radars or multiple sensors located at different locations. The sensing and tracking module determines the spatial location of the to-be-heated object based on the information gained by the radars or the sensors and ensures the length in the at least one dimension of the object to-be-heated.

The control module adjusts light direction of the light source module toward the object to-be-heated based on the spatial location of the object to-be-heated and regulates the light emission beam angle of the light from the light source module along the length in at least one dimension of the object to-be-heated so sensed by the sensing and tracking module so that the light source module is able to emit light in a certain beam angle to match with the length in the at least one dimension of the object to-be-heated.

Preferably, the heating system includes a temperature sensing module for sensing temperature of the object to-be-heated and a control module can reduce the output power or stop operation of the light source module once the object to-be-heated reaches a previously determined temperature.

Preferably, the temperature sensing module also includes at least one movable temperature detecting device with adjustable temperature detection direction and responsible for informing the control module to stop or reduce the output power of the light source module once the object to-be-heated reaches a previously determined temperature.

Preferably, the control module can also increases the power of the light source module if the at least one temperature detecting device detects that the temperature of the object to-be-heated is below a target value and temperature difference therebetween reaches a previously determined value.

Preferably, at least one temperature detecting device has a distance detecting unit responsible for detection of the distance between the object to-be-heated and the temperature detecting device so that the preprogrammed output power calculation formula in the control module is able to adjust the power of the light source module to correspond to the distance between the temperature detecting device and the object to-be-heated, the detected object temperature and a preprogrammed object's target temperature.

Preferably, the light source module also includes a power management device. The light source module is an infrared LED chip system and the power management device is responsible for supplying and regulating output power to the infrared LED chip.

Preferably, the heating system also includes a remote control device to send the information of target temperature, change of the target temperature, power of the light source and/or signals responsible for regulating the change of the light source's output power to the control module.

Preferably, the control module includes a communication interface. The remote control device sends the control signal to the control module and the control signal is sent via WiFi, ZigBee or wire for communication.

Preferably, the light source module has a light source matrix and a lens or a lens set in front of the light source matrix.

Preferably, the heating system of the embodiment of the present invention also includes an object temperature detecting module for detection of the temperature of the object. The control module also increases the power output of the light source when the temperature detected by the temperature detecting device is below a target temperature value.

A bed is provided, which includes a board, a rail and a heating system described above. The rail surrounds at least a portion of the board. A previously reserved area is formed on top of the board. The sensing and tracking module and the light source module are provided on top of the rail.

Another kind of bed is provided with a board, a bracket and the heating system. Each end of the bracket is securely attached to an edge of the board and extends upward to the top of the board. A reserved area is on top of the board and the sensing and tracking module as well as the light source module are put higher than the board.

The embodiment of the present invention also includes a heating system characterized in that the heating system includes:

a light source module having at least one light source emitting light toward the object-to-be heated;

an object temperature detecting module for detecting temperature of the object-to-be heated;

a control module to reduce output power of the light source when the detected temperature of the object-to-be heated by the object temperature detecting module reaches a temperature value, and to increase output power of the light source when the temperature of the object-to-be heated by the object temperature detecting module is below a temperature target and when temperature difference between the temperature of the object-to-be heated and the temperature target reaches a previously determined value.

Preferably, the light source module has a lens or a lens set. The lens or the lens set is used to make the light from the light source for heating emitted in a designated angle or a designated intensity distribution pattern.

Preferably, the light from the light source module forms a Batwing pattern.

Preferably, the light from the light source for heating is emitted by an infrared LED chip.

Preferably, the emitting direction of the light from the light source module for heating is adjustable so that the light from the light source module is able to be directed to heat the object-to-be heated.

Preferably, the wavelength of the light for heating from the light source module is between 900 nm-5000 nm.

Preferably, the heating system also includes a remote control device to send control signals representing target temperature, variations of the target temperature, output power of the light source for heating and/or variations of the output power of the light source for heating.

The preferred embodiments described above may be randomly combined to achieve the utmost performance in accordance with knowledge well known in the art.

It is noted that the characteristic advantages of the preferred embodiments of the present invention includes the following.

The heating system and the bed with the heating system are able to automatically adjust power output according to physical characteristics of the object to-be-heated so as to minimize the possibility to heat unrelated object(s), space and ensure high energy age efficiency.

BRIEF DESCRIPTION OF THE DRAWINGS

FIG. 1 is an exploded perspective view of the parts of the heating system of the preferred embodiment of the present invention.

DETAILED DESCRIPTION OF THE PREFERRED EMBODIMENT

Preferred embodiment(s) of the present invention in combination with the attached drawings shall be provided in detail in the following description. However, the given description is for example purpose only and should not be deemed as a limiting to the scope of the present invention in any way.

In order to make it easy to carry out the preferred embodiment of the present invention, a detailed description of the parts of the invention, supported with figures is provided here. As each part of the preferred embodiment of the present invention has many features, it is made easy to read, by referring to each feature with a number included in the parts description text. The number of the parts feature(s) is indicated here by starting it sequentially from the number 1, wherever a part feature appears in a text, it is directly assigned its associated serial number.

It is to be noted that the heating system of the preferred embodiment of the present invention includes a sensing and tracking module, a light source module and a control module and the system is expected to raise temperature of an object which is not able to move within a large area. Comparatively speaking, the heating system of the preferred embodiment of the present invention has great advantage in energy saving compared to the conventional art.

The sensing and tracking module is used to detect the length in at least one dimension of the object to-be-heated. The object may be movable or kept still within a predetermined area. The light source module includes at least one light source that can tune its light emitting direction and can also change its beam angle for heating along at least one dimension. As the object is kept within a predetermined area or even basically still, the light source is aiming substantially toward the predetermined area, i.e., the object and is free to change its lighting direction. The control module regulates the light source for heating according to the length sensed by the sensing and tracking module along at least one dimension of the object to ensure that the light intensity distribution as well as beam angle of the light from the light source matches with the object in that dimension.

The word "dimension" includes not only the typical linear direction, it also covers a nonlinear direction of a certain coordinate in a space. In some embodiments, the sensing and tracking module may sense multiple lengths of an object in multiple dimensions which may form completely or at least portions of the physical characteristics of the object to be heated. For example, if the object to-be-heated is a cylinder, the sensing and tracking module is able to sense the length of the cylinder and a respective length in two perpendicular directions of the cylinder's cross-section to determine roughly the shape of the object. Based on the gained information, the control module is able to regulate the light source for heating in multiple dimensions to ensure the light intensity and light beam from the light source will match with shape of the object. When talking about the word "match", it means the regulated light beam from the light source for heating projects substantially on areas of the object and avoids areas or objects other than the target object.

In a simpler embodiment, the sensing and tracking module is able to sense the length of the object to-be-heated in certain direction and the control module can regulate the light beam angle from the light source for heating to ensure the light beam angle as well as the light intensity match with the length of the object in that direction. In other embodiment, the sensing and tracking module is able to sense the lengths of the object in two directions, for example, the lengths in two mutually perpendicular directions so that the scale and dimension of the object in a certain plane is obtained to a certain degree so that the control module can regulate the light beam angle of the light source accordingly. Certainly, if some of the currently commercially available sensing and tracking technology is applied, some physical characteristics, e.g., shape(s) in a certain dimension and/or overall appearance of the object may also be obtained. In this embodiment, the lengths of the object are sensed in multiple dimensions, which is also applicable.

Basically, the heating system of the preferred embodiment of the present invention projects a large portion of the energy on the needed object via light and avoids light toward objects or spaces other than the target object so as to increase energy efficiency.

Using the aforementioned method to heat up the object, generally, it is required to obtain the lengths of the object in multiple dimensions when the shape of the object is complex so as to properly regulate the light beam angle of the light source. However, to an object having a simple or regular geometric shape, e.g., column, rectangle, sensing its lengths in no more than three dimensions is able to obtain enough information about the physical characteristics of the object to regulate the light beam angle to have great energy saving effect. In order to have higher energy efficiency, radars or multiple sensors in multiple locations may also be applicable to have accurate physical characteristics of the object so that the control module is able to regulate the light source module accordingly.

The light beam angle adjustment may also be accomplished by a lens or a lens set of the light source module. That is, the control module may control the light for heating from the light source module via secondary optics to regulate the light's beam angle, intensity distribution as well as the direction. Of course, the regulation to the light for heating via the lens or the lens set may incorporate with the light source to accomplish the same goal. In some of the typical embodiments when the light source module has the lens or the lens set, the light beam from the light source for heating is formed into a specific angle and intensity. For example, when the object to-be-heated has physical characteristics like a cylinder or a shape having two thinner opposite ends and a thicker central part, the light beam pattern may have higher intensity in both sides of the light beam, which may greatly reduce energy loss or energy consumption during heating process and achieve the goal of better heating uniformity. To this point, it is advantageous in the experiment on human body heating. For example, when the light beam for heating is projecting on human body, the lateral direction on human body or in the direction toward the width of the chest, the light beam as well as the intensity of the light may scatter into a Batwing pattern in order to have better heating effect on human body and arms so that uneven heating on human body may not occur and the subject, human body, may thus experience comfort during the entire heating process.

The arrangement of the lens or the lens set may be designed depending on various situations. One typical arrangement is that there are different types of lenses in the heating system to achieve different requirements for light beam intensity. When targeting different shapes of objects for heating, different lens or a lens set may be employed in front of the light source for heating to form different light distribution, such as batwing shape or Lambertian light distribution. Relative location adjustment between lenses in the lens set may also be used to accomplish the requirements for multiple intensity requirements. And the relative location adjustment between lenses in the lens set may be realized by the power device or driving motor device in the heating system.

On the other hand, in the selection of light source for heating, it may be dependent on the absorption characteristics of the object to-be-heated. Therefore, the light source for heating may be a light emitting diode (LED), an incandescent, a Halogen lamp, a Florescent light-tube, a gas-discharge lamp or a light source emitting electromagnetic wave with some wavelengths being filtered. In some embodiments, the light source for heating may be changeable depending on the object to-be-heated.

In the case when the human body is taken into consideration, the wavelength of the light source for heating falls in the range between 900 nm-5000 nm, which would have better heating effect if the LED chip is adopted as for the light source for heating. When the object to-be-heated is determined, the LED with the right wavelength depending on the absorption characteristics of the object shall be selected. However, if a proper light source may not be found based on the absorption spectrum characteristics of the object to-be-heated, a coating material having the characteristic for absorbing the electromagnetic wave of the known light source may be applied on the surface of the object to increase the heating effect.

In some embodiments of the present invention, the sensing and tracking module has a distance measuring unit for measuring the distance between the light source for heating and the object to-be-heated. The control module calculates the light beam angle matching the light from the light source in accordance with the distance and the length in at least one dimension of the object to-be-heated and thus regulates the light source to meet with the angle requirement. In some of the embodiments, in order to have better heating uniformity, the control module calculates the light intensity distribution to achieve the goal of even heating according to the length in at least one dimension of the object and the distance between the object and the light source and thus adjusts or regulates the light source or the lens or lens set to reach the intensity distribution requirement.

In some embodiments targeting on human body heating, in order to maintain energy conservation as well as the comfort and safety of the human body during and after the heating process, a target temperature detecting module for detecting temperature of the object to-be-heated is added to the heating system. The control module reduces the light output power or stops the operation of the light source for heating to conserve energy and avoid over heating when the target temperature detecting module detects that the temperature of the object reaches a previously determined value. By doing this, one can prevent or avoid bad overheating result, such as the discomfort or even possible danger during the heating process. Furthermore, when the target temperature detecting module detects the temperature of the object to-be-heated is below a previously determined value, i.e., threshold value, the output power of the light source for heating will be increased. When the to-be-heated object is far away from the light source, the heating speed can be increased by changing the light power. The target temperature detecting module may adopt a temperature sensor such as an infrared sensor.

It is to be noted that the distance measuring unit in the heating system, for example, may be any type of distance detecting device in the sensing and tracking module to sense the object to-be-heated, such as radar or an infrared sensor. In some of the embodiments, a proper sensor, such as an infrared sensor, may provide both the temperature and distance sensing function.

In some of the embodiments, an output power formula is preprogrammed in the control module to regulate output power of the light for heating based on the detected temperature of the object, distance to the object as well as the wanted target temperature.

In some of the embodiments, the light source module may include a power management device to provide power to, for example, the infrared LED chips as the light source as well as regulate the output power by tuning the duty cycle of the output current to the infrared LED chips. That is, the power management device adopts a pulse width modulation to regulate or modulate the output power of the infrared LED chip. By doing this, it is possible to gradually regulate or modulate the output power of the light source. For example, each time 1% of the output power of the light source may be increased or reduced according to requirements.

In some human body heating embodiments, in order to have control or regulate the heating system of the preferred embodiment of the present invention according to user's self-feeling, the heating system also includes a remote-control device to send control signals like wanted target temperature, variations of the target temperature, output power of the light source for heating and/or variations of the output power of the light source for heating. The remote control device may be a device equipped with a mobile terminal having therein a communication module, such as a cellphone or the like. The user may use the cellphone to provide the expected skin temperature and also the acceptable skin temperature range and response time. The control module receives the signal sent from the cellphone wirelessly and proceeds with the regulation or modulation of the heating process. It is to be noted that currently commercially available communication devices, contents, communication protocols may all be incorporated with the embodiments of the present invention. In other embodiments, receiving and sending the control signals are done via wires or cables and still in embodiments, the control signals are sent and received via wireless communication, such as Bluetooth, Wi-Fi, ZigBee or the like.

In some embodiments of the present invention, the light source for heating in the heating system may be arranged into a matrix and there may be a lens or a lens set provided in front of the light source.

Embodiment 2

In this embodiment, a bed is provided and can be heated by the previously introduced heating system. The bed includes a board, a rail and the heating system. The rail surrounds at least a portion of the board which defines therein a preserved area on top thereof. All the elements, parts or devices of the heating system are provided on top of a portion of the rail. In some embodiment, the elements from the light source module are provided on side of the bed and on top of the rail to enable the light source for heating toward the center of the board.

In one embodiment of the present invention, with reference to FIG. 1, the heating system also includes two brackets 4 and a casing composed of a top casing 2a, a middle casing 2b with holes in two opposite sides thereof and a bottom casing 2c. The casing encloses therein all the elements of the sensing and tracking module, the control module 3 as well as the light source module 1 (including the light source 11 and the lens 12 in front of the light source) so as to form a body. Each of the two brackets 4 has a substantially U shaped bottom 41 and a L shaped linkage 42 one end of which is securely connected to a top of the U shaped bottom 41 and the other end of which is inserted into the corresponding hole defined in the side of the middle casing 2b such that the entire casing is pivotally connected between the two brackets 4 via the respective linkage 42. The U shaped bottom 41 may then be mounted on the lateral rail of the bed via any suitable fastening devices, i.e., a fastener, a clamp or the like. Multiple light sources 11 of the light source module 1 are arranged as a matrix. As the casing is pivotally connected to the two brackets 4, the orientation of the light source matrix is adjustable. The adjustment of the orientation of the light source matrix maybe processed via manual or any mechanical devices such as a gear set and/or an electrical motor device to drive the casing to pivot. These motor driving devices are all controlled by the control module to drive the casing toward a specific direction.

In one embodiment of the present invention, the temperature of the bed will be controlled by the heating system. When the heating system detects there is a human body lying on the bed, the heating system starts its operation and periodically detects the human body temperature. In one embodiment of the present invention, when the human body temperature detected is below a previously determined value, the heating system increases the output power of the light source and when the human body temperature detected reaches or is larger than the previously determined value, the heating system reduces the output power of the light source.

Thus, it is obvious that the embodiment of the present invention is able to maintain the human body temperature at almost a constant value and simultaneously provide comfort, safety and great energy conversation.

In still another preferred embodiment of the present invention, the bed is a baby-crib and the heating system is mounted on the guardrail of the crib to be away from the crib board. The light source for heating is an infrared LED chip to emit light with a Batwing light distribution. The light intensity distribution and the beam angle are determined by the distance from the heating system to the baby and also determined by the shape of the baby's chest so that the heating system is able to achieve the best light intensity distribution to ensure the baby is evenly warmed.

In still another embodiment of the present invention, the bed also includes a bracket one end of which is securely attached to an edge of the board and the other end is extending upward from the board and all the elements of the sensing and tracking module as well as the light source module are mounted on the free end of the bracket to be away from the board of the bed.

Embodiment 3

The heating system is substantially the same as previously described in embodiment 1 and has only the following difference.

In this embodiment, the object to-be-heated is not almost immovable within a preserved area but movable within a previously determined area. For example, the object may be a person within a room, a bus waiting room, a train platform, a stairway or any open space. In order to have high heating efficiency to the movable object, the sensing and tracking module includes at least one radar or sensors mounted at different locations to receive information regarding the object's location as well as the length in at least one dimension. In another embodiment of the present invention, the sensing and tracking module is able to have precise location and physical appearance of the object (person) in the space via radar or sensor(s).

The control module adjusts orientation of the light source for heating toward the object according to the object's spatial position and then regulates the light source for heating to emit light in an angle matching with the length in at least one dimension of the object. Furthermore, the control module is able to regulate the light source for heating to emit light in a pattern suitable for the appearance of the object.

The heating system in the embodiments of the present invention may be applied in a room, a bus waiting room, a train platform, a stairway or any open space to directly project light source for heating on the person(s) in these spaces without heating the entire space, which greatly reduces energy loss and provides comfort to the person experiencing the benefit of the heating system.

After a detailed description of the preferred embodiment(s) has been provided, any skilled person in the art would easily understand the description so provided is for example purpose only. The scope for protection of the present invention is defined by the attached claims. Any skilled person in the art would easily amend, modify or alter the elements/devices of the present invention without departing from the principle essence and spirit of the present invention. However, the amendment, modification or alteration shall fall within the protection scope sought of the present invention.

What is claimed is:

1. A heating system comprising:
    a sensing and tracking module to sense a length in at least one dimension of an object to-be-heated in a previously determined area;
    a light source module having at least one light source that changes its lighting direction and changes its beam angle along the at least one dimension;
    a temperature sensing module for sensing temperature of the object to-be-heated and reducing an output power or stop operation of the light source module once the object to-be-heated reaches a previously determined temperature, wherein the temperature sensing module includes at least one movable temperature detecting device with adjustable temperature detection direction and is responsible for stopping or reducing the output power of the light source module once the object to-be-heated reaches a previously determined temperature; and
    a control module for regulating light emitted by the light source module onto the to-be heated object along the at least one dimension to match with the length of the to-be-heated object based on the length sensed by the sensing and tracking module.

2. The heating system as claimed in claim 1, wherein the light source module has a lens or a lens set for shaping the light from the light source into a desired shape and/or intensity distribution.

3. The heating system as claimed in claim 2, wherein the sensing and tracking module has a distance measuring unit for measuring a distance between the object to-be-heated and light source for heating and the control module regulates a light beam angle from the light source in accordance with the length sensed by the sensing and tracking module in at least one dimension of the object to-be-heated as well as the distance to allow the light source for heating to emit light in an angle matching with the object to-be-heated in at least one dimension.

4. The heating system as claimed in claim 2, wherein the intensity distribution is a Batwing beam pattern or Lambertian pattern.

5. The heating system as claimed in claim 2, wherein a wavelength of the light for heating from the light source module is between 900nm-5000nm.

6. The heating system as claimed in claim 5, wherein the light source module is an infrared light emitting diode chip.

7. The heating system as claimed in claim 3, wherein the control module calculates the intensity distribution to evenly heat the object to-be-heated based on the length in at least one dimension of the object to-be-heated and the distance between the object to-be-heated and the light source module, which are sensed by the sensing and tracking module, and regulates the light source and/or lens or lens set to reach the desired light intensity distribution.

8. The heating system as claimed in claim 1, wherein the object to-be-heated is movable and the sensing and tracking module includes a radar or multiple sensors located at different locations, the sensing and tracking module determines a spatial location of the object to-be-heated based on sensed information gained by the radar or the sensors and ensures the length in the at least one dimension of the object to-be-heated,
    the control module adjusts orientation of the light source for heating toward the object to-be-heated in accordance with the spatial location thereof and regulates the light source for heating according to the length in the at least one dimension of the object to-be heated so sensed by the sensing and tracking module to allow light from the light source module to have an angle matching with the length in the at least one dimension of the object to-be-heated.

9. The heating system as claimed in claim 1, wherein the control module also increases the output power of the light source module if the at least one temperature detecting device detects that the temperature of the object to-be-heated is below the previously determined temperature and temperature difference between the temperature of the object-to-be heated and the previously determined temperature reaches a previously determined value.

10. The heating system as claimed in claim 1, wherein the at least one temperature detecting device has a distance detecting unit responsible for detection of the distance between the object to-be-heated and the temperature detecting device so that a preprogrammed output power calculation formula in the control module is able to adjust the power of the light source module to correspond to the distance between the temperature detecting device and the object to-be-heated, the detected temperature and a preprogrammed target temperature.

11. The heating system as claimed in claim 1, wherein the light source module includes a power management device, the light source module is an infrared LED chip and the power management device is responsible for supplying and regulating power to the infrared LED chip.

12. The heating system as claimed in claim 10, wherein the heating system also includes a remote control device to send the target temperature, variations of the target temperature, the output power of the light source and/or signals responsible for regulating the output power of the light source to the control module.

13. The heating system as claimed in claim 12, wherein the control module includes a communication interface sending a control signal to the control module and the control signal is sent via WiFi, ZigBee or wire.

14. The heating system as claimed in claim 12, wherein the light source module has a light source matrix and a lens or a lens set in front of the light source matrix.

15. The heating system as claimed in claim 8 further having an object temperature detecting module to detect temperature of the object-to-be heated, wherein the control module increases output power of the light source for heating when the detected temperature is below a target value.

16. A bed comprising a board, a rail and the heating system as claimed in claim 1, wherein the rail surrounds at least a portion of the board, a previously reserved area is formed on top of the board, elements of the sensing and tracking module and the light source module are securely provided on a portion of the rail.

17. A bed comprising a board, a bracket and the heating system as claimed in claim 1, wherein one end of the bracket is securely attached to an edge of the board and extends upward to a top of the board, a reserved area is on the top of the board and elements of the sensing and tracking module and the light source module are securely provided on a portion of the bracket.

* * * * *